United States Patent
Riedel et al.

(12) 
(10) Patent No.: US 6,558,680 B1
(45) Date of Patent: May 6, 2003

(54) COSMETIC AND DERMATOLOGICAL PREPARATIONS BASED ON O/W EMULSIONS

(75) Inventors: Heidi Riedel, Hamburg (DE); Günther Schneider, Hamburg (DE); Gunhild Hamer, Hamburg (DE); Andreas Bleckmann, Ahrensburg (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 09/621,240

(22) Filed: Jul. 26, 2000

(30) Foreign Application Priority Data

Jul. 26, 1999 (DE) .......................... 199 34 944

(51) Int. Cl.⁷ ............. A61K 6/00; A61K 7/00; A61K 81/21; A61K 31/08; A61K 31/045; A61K 31/01; A01N 37/00; A01N 31/14; A01N 31/00; A01N 31/02

(52) U.S. Cl. ................. 424/401; 514/506; 514/723; 514/724; 514/762; 514/938

(58) Field of Search ............. 424/401, 78.02, 424/78.03; 514/506, 723, 724, 762, 938, 944

(56) References Cited

U.S. PATENT DOCUMENTS

| | | | |
|---|---|---|---|
| 5,482,704 A | | 1/1996 | Sweger et al. |
| 5,560,904 A | * | 10/1996 | Laugier et al. ........... 424/78.08 |
| 5,560,916 A | | 10/1996 | Koulbanis et al. |
| 5,723,109 A | | 3/1998 | Causse et al. |
| 5,753,109 A | | 5/1998 | Ascione et al. |
| 5,795,575 A | | 8/1998 | Bombardelli et al. |
| 5,863,545 A | * | 1/1999 | Griat ..................... 424/401 |
| 5,932,608 A | | 8/1999 | Nguyen et al. |

FOREIGN PATENT DOCUMENTS

| | | |
|---|---|---|
| EP | 0 681 830 A1 | 5/1995 |
| EP | 0 914 815 A1 | 5/1999 |

OTHER PUBLICATIONS

Patent Abstracts of Japan, Publication No. 10330244 A, published Dec. 15, 1998.
Patent Abstracts of Japan, Publication No. 09175987 A, published Jul. 8, 1997.
Patent Abstracts of Japan, Publication No. 09175986 A, published Jul. 8, 1997.
Patent Abstracts of Japan, Publication No. 09143048 A, published Jun. 3, 1997.
Patent Abstracts of Japan, Publication No. 09095415 A, published Apr. 8, 1997.
Patent Abstracts of Japan, Publication No. 07233046 A, published Sep. 5, 1995.
Patent Abstracts of Japan, Publication No. 06329621 A, published Nov. 29, 1994.
Patent Abstracts of Japan, Publication No. 61069707 A, published Apr. 10, 1986.

* cited by examiner

*Primary Examiner*—Sreeni Padmanabhan
*Assistant Examiner*—Lauren Q. Wells
(74) *Attorney, Agent, or Firm*—Norris McLaughlin & Marcus

(57) ABSTRACT

Stable, biocompatible cosmetic or dermatological oil-in-water emulsions (I), containing fatty acids and alcohols, glycerides, ethoxylated esters, non-polar lipids and consistency components, are new. Cosmetic or dermatological oil-in-water emulsion preparations (I) contain (by weight): (a) 0.1–5% 14–22 C fatty acid(s); (b) 0.2–10% fatty acid mono- and/or diglyceride(s); (c) 0.1–5% ethoxylated fatty acid ester(s); (d) 0.5–10% non-polar lipid(s); (e) 0.5–7.5% fatty alcohol(s); and (f) 0.5–7.5% lipophilic consistency source(s) having a melting point or drop point of at least 30 degrees C. The sum of the contents of (a)–(c) is at most 12% and the lipid phase optionally contains up to 40% (based on this phase) of polar lipids.

10 Claims, No Drawings

COSMETIC AND DERMATOLOGICAL PREPARATIONS BASED ON O/W EMULSIONS

The present invention relates to cosmetic and dermatological emulsions, in particular skincare cosmetic and dermatological emulsions. In a preferred embodiment, the present invention relates to a use which permits the stability of electrolyte-containing preparations, in particular emulsions, preferably of O/W emulsions, to be increased.

The skin is the largest human organ. Amongst its many functions (for example for temperature regulation and as a sensory organ) the barrier function, which prevents the skin (and ultimately the entire organism) from drying out, is by far the most important. At the same time, the skin acts as a protective device against the penetration and absorption of external substances. This barrier function is effected by the epidermis, which, as the outermost layer, forms the actual protective sheath against the environment. Being about one tenth of the total thickness, it is also the thinnest layer of the skin.

The epidermis is a stratified tissue in which the outer layer, the horny layer (Stratum corneum), is the part which is of significance for the barrier function. The Elias skin model, which is currently recognized in the specialist field (P. M. Elias, *Structure and Function of the Stratum Corneum Permeability Barrier, Drug Dev. Res.* 13, 1988, 97–105), describes the horny layer as a two-component system, similar to a brick wall (bricks and mortar model). In this model, the horny cells (corneocytes) correspond to the bricks, and the lipid membrane in the intercellular spaces, which is of complex composition, corresponds to the mortar. This system is essentially a physical barrier to hydrophilic substances, but, because of its narrow and multilayered structure, can equally, however, also be passed by lipophilic substances only with difficulty.

The present invention relates, in a particular embodiment, to cosmetic or pharmaceutical preparations having a reduced feel of stickiness, to processes for their preparation, and the use of active ingredients for reducing the feel of stickiness of cosmetic preparations.

Apart from its barrier action against external chemical and physical influences, the epidermal lipids also contribute to the holding together of the horny layer and have an effect on the smoothness of the skin. In contrast to the sebaceous gland lipids, which do not form a continuous film on the skin, the epidermal lipids are distributed over the entire horny layer.

The extremely complex interaction of the moisture-binding substances and of the lipids of the upper layers of the skin is very important for the regulation of skin moisture. For this reason, cosmetics generally comprise, in addition to balanced lipid mixtures and water, water-binding substances.

As well as the chemical composition, however, the physical behavour of these substances is also of importance. The development of very biocompatible emulsifiers and surfactants is therefore desirable. Products formulated therewith aid the liquid-crystalline organization of the intercellular lipids of the Stratum corneum, thereby improving the barrier properties of the horny layer. It is particularly advantageous if their molecular constituents consist of substances which are naturally occurring in the epidermis.

Cosmetic skin care primarily means that the natural function of the skin as a barrier against environmental influences (e.g. dirt, chemicals, microorganisms) and against the loss of endogenous substances (e.g. water, natural fats, electrolytes) is strengthened or rebuilt.

If this function is impaired, increased resorption of toxic or allergenic substances or attack by microorganisms may result, leading to toxic or allergic skin reactions.

Another aim of skin care is to compensate for the loss by the skin of lipids and water caused by daily washing. This is particularly important when the natural regeneration ability is insufficient. Furthermore, skincare products should protect against environmental influences, in particular against sun and wind, and delay skin ageing.

Medicinal topical compositions generally comprise one or more medicaments in an effective concentration. For the sake of simplicity, in order to distinguish clearly between cosmetic and medicinal use and corresponding products, reference is made to the legal provisions in the Federal Republic of Germany (e.g. Cosmetics Directive, Foods and Drugs Act).

Customary cosmetic forms of application are emulsions. This term generally means a heterogeneous system of two liquids which are immiscible or miscible only to a limited extent with one another, which are usually referred to as phases. One is in the form of droplets (disperse or internal phase), whilst the other liquid forms a continuous (coherent or internal) phase. Less common forms of application are multiple emulsions, i.e. those which, in the droplets of the dispersed (or discontinuous) phase, comprise for their part droplets of a further dispersed phase, e.g. W/O/W emulsions and O/W/O emulsions.

More recent findings have recently led to a better understanding of cosmetic emulsions which are of relevance in practice. Here, it is assumed that the emulsifier mixtures used in excess form lamellar liquid-crystalline phases or crystalline gel phases. In the gel network theory, stability and physicochemical properties of such emulsions are attributed to the formation of viscoelastic gel networks.

In order to be able to ensure the metastability of emulsions, interface-active substances, i.e. emulsifiers, are usually necessary. The use per se of customary cosmetic emulsifiers is entirely acceptable. Nevertheless, emulsifiers, as ultimately any chemical substance, may in certain cases cause allergic reactions or reactions based on oversensitivity of the user. For example, it is known that in some particularly sensitive people, certain light dermatoses are triggered by certain emulsifiers and simultaneous action of sunlight.

It is possible to prepare emulsifier-free preparations which, for example, have, in an aqueous phase, dispersed oil droplets, similar to an O/W emulsion. A prerequisite for this may be that the continuous aqueous phase has a gel framework which stabilizes the dispersed phase, and other conditions besides. Such systems are sometimes called hydrodispersions or oleodispersions depending on which is the disperse phase and which is the continuous phase.

For cosmetic technology, it is, however, neither necessary nor possible to dispense with emulsifiers altogether, especially since there is a certain choice of particularly mild emulsifiers. However, the prior art lacks a satisfactorily broad range of such emulsifiers which would then also significantly broaden the application spectrum of correspondingly mild cosmetic preparations which are tolerated by the skin.

An object of the present invention was therefore to provide cosmetic and dermatological preparations having excellent skincare properties.

A disadvantage, in particular of O/W emulsions, is often their inadequate stability to relatively high electrolyte concentrations, which manifests itself in phase separation. This can indeed sometimes lead to problems, even in the case of W/O emulsions, although this is by no means as important here as in the case of O/W systems. Although these can often be remedied to a certain extent through appropriate choice of the emulsifier system, other disadvantages, however, arise just as often.

On the other hand, it is often desireable to use certain electrolytes in order to be able to utilize their other physical, chemical or physiological properties.

The concentrations of all of the constituents of a cosmetic or dermatological preparation are usually chosen in units such as % by weight, mol % and the like. In view of their greater or lesser dissociation into cations and anions, often in several dissociation stages, it sometimes appears more advantageous for the description of the present invention and its technical background, to start from the ionic strength of a given electrolyte in its solution.

The ionic strength I of an electrolyte solution is defined as $$I = 1/2 \sum_i c_i z_i^2$$

where $c_i$ or the concentrations of the individual types of ion (in mol/l) and $z_i$ are their charges. The physical unit of ionic strength is that of a concentration (mol/l).

For example, a 1% strength (=0.17 molar) sodium chloride solution has an ionic strength I=0.17.

Another object of the present invention was therefore to discover ways of producing cosmetic or dermatological emulsions, in particular O/W emulsions, which are stable to increased electrolyte concentrations—or increased ionic strengths.

It was furthermore an object of the present invention to provide preparations which significantly improve the condition of the skin, in particular reduce skin roughness.

It is known that certain substances, for example a few selected powder raw materials, in particular talc, can be added to reduce a feeling of stickiness and also a feeling of greasiness. However, apart from the fact that this is only rarely completely successful, such an addition also changes the viscosity of the product in question and lowers the stability.

The object was therefore to remedy all of these disadvantages of the prior art. In particular, the intention was to provide products having reduced stickiness or greasiness. Products in the field of care cosmetics, decorative cosmetics and pharmacological technology should likewise be freed from the described disadvantages of the prior art.

Furthermore, it was an object of the invention to develop cosmetic bases for cosmetic preparations which are characterized by good skin compatibility.

Furthermore, it was an object of the present invention to provide products with as broad an application diversity as possible. For example, the intention was to provide bases for preparation forms such as cleansing emulsions, face and bodycare preparations, and also distinctly medicinal-pharmaceutical administration forms, for example preparations for treating acne and other skin conditions.

Surprisingly, it has been found, and herein lies the solution to these problems, that cosmetic and dermatological preparations in the form of O/W emulsions, comprising (1) 0.1 up to 5% by weight, based on the total weight of the preparations, of one or more $C_{14}$–$C_{22}$-fatty acids, (2) 0.2 up to 10% by weight, based on the total weight of the preparations, of one or more mono- and/or diglycerides of fatty acids, (3) 0.1 up to 5% by weight, based on the total weight of the preparations, of one or more ethoxylated fatty acid esters, where the sum of (1), (2) and (3) is at most 12% by weight, (4) 0.5 to 10% by weight, based on the total weight of the preparations, of one or more nonpolar lipids, (5) 0.5–7.5% by weight, based on the total weight of the preparations, of one or more fatty alcohols (6) 0.5–7.5% by weight, based on the total weight of the preparations, of one or more lipophilic bodying agents having a melting point or dropping point of $\geq 30°$ C.

(7) where the total lipid phase can comprise up to 40% by weight of polar lipids, based on the total weight of the lipid phase, overcome the disadvantages of the prior art.

It was therefore not foreseeable by the person skilled in the art that the preparations according to the invention would be more effective moisture-donating preparations, better promote skin smoothing, be characterized by better care action, be better vehicles for cosmetic and medicinal-dermatological active ingredients have higher stability to decomposition in oil and water phases and would be characterized by better biocompatibility would be characterized by better feel on the skin and by higher cosmetic elegance than the prior art preparations.

The preparations according to the invention can be formulated both in flowable form and also in cream form, have very good cosmetic properties, in particular with regard to stickiness, and have very good skin compatibility and skincare performance.

Advantageous embodiments of the present invention relate to cosmetic and dermatological preparations according to the main claim, comprising (1) 0.5 up to 1.0% by weight, based on the total weight of the preparations, of one or more $C_{14}$–$C_{22}$-fatty acids.

Advantageous embodiments of the present invention also relate to cosmetic and dermatological preparations according to the main claim, comprising (2) 2.5 up to 3.0% by weight, based on the total weight of the preparations, of one or more mono- and/or diglycerides of fatty acids.

Advantageous embodiments of the present invention also relate to cosmetic and dermatological preparations according to the main claim, comprising (3) 1.0 up to 1.5% by weight, based on the total weight of the preparations, of one or more ethoxylated fatty acid esters.

Particularly advantageous embodiments of the present invention are obtained if they relate to cosmetic and dermatological preparations according to the main claim, comprising (2) up to 10% by weight, based on the total weight of the preparations, of glyceryl stearate.

Particularly advantageous embodiments of the present invention are obtained when they relate to cosmetic and dermatological preparations according to the main claim, comprising (3) up to 5% by weight, based on the total weight of the preparations, of one or more ethoxylated fatty acid esters chosen from the group of polethylene glycol-20 (PEG-20) to polethylene glycol-100 (PEG-100) stearates.

It is particularly advantageous to choose weight ratios between the constituents given under (1), (2) and (3) of approximately 1:4:2.

(5) 0.5 to 10% by weight, based on the total weight of the preparations, of one or more nonpolar lipids, chosen from the group of mineral oil and/or mineral waxes (including Vaseline).

Furthermore, advantageous embodiments of the present invention are obtained if these relate to cosmetic and dermatological preparations according to the main claim, comprising (6) 2.0–3.0% by weight, based on the total weight of the preparations, of one or more fatty alcohols.

Furthermore, advantageous embodiments of the present invention are obtained if these relate to cosmetic and dermatological preparations according to the main claim, comprising (7) 1.5–2.5% by weight, based on the total weight of the preparations, of one or more lipophilic bodying agents having a melting point or dropping point of ≧30° C.

For the purposes of the present disclosure, the general term for fats, oils, waxes and the like which is sometimes used is the expression "lipids", with which the person skilled in the art is entirely familiar. The terms "oily phase" and "lipid phase" are also used synonymously.

Oils and fats differ from one another in their polarity, which is difficult to define. It has already been proposed to adopt the interfacial tension towards water as a measure of the polarity index of an oil or of an oily phase. Then, the lower the interfacial tension between this oily phase and water, the greater the polarity of the oily phase in question. According to the invention, the interfacial tension is regarded as one possible measure of the polarity of a given oil component.

The interfacial tension is the force which acts on an imaginary line one meter in length in the interface between two phases. The physical unit for this interfacial tension is conventionally calculated from the force/length relationship and is usually expressed in mN/m (millinewtons divided by meters). It has a positive sign if it endeavors to reduce the interface. In the converse case, it has a negative sign. For the purposes of the present invention, lipids are regarded as polar if their interfacial tension towards water is less than 30 mN/m.

Polar oils are for example those from the group of lecithins and of fatty acid triglycerides, namely the triglycerol esters of saturated and/or unsaturated, branched and/or unbranched alkanecarboxylic acids having a chain length of from 8 to 24, in particular 12 to 18, carbon atoms. The fatty acid triglycerides can, for example, advantageously be chosen from the group of synthetic, semisynthetic and natural oils, such as, for example, olive oil, sunflower oil, soya oil, peanut oil, rapeseed oil, almond oil, palm oil, coconut oil, castor oil, wheatgerm oil, grapeseed oil, thistle oil, evening primrose oil, macadamia nut oil and the like.

Other polar oil components can be chosen from the group of esters of saturated and/or unsaturated, branched and/or unbranched alkanecarboxylic acids having a chain length of from 3 to 30 carbon atoms and saturated and/or unsaturated, branched and/or unbranched alcohols having a chain length of from 3 to 30 carbon atoms, and from the group of esters of aromatic carboxylic acids and saturated and/or unsaturated, branched and/or unbranched alcohols having a chain length of from 3 to 30 carbon atoms. Such ester oils can then advantageously be chosen from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semisynthetic and natural mixtures of such esters, such as, for example, jojoba oil.

In addition, the oily phase can be advantageously chosen from the group of dialkyl ethers, the group of saturated or unsaturated, branched or unbranched alcohols. It is particularly advantageous if the oily phase of the W/O emulsions according to the invention contains $C_{12-15}$-alkyl benzoate or consists entirely of the latter.

Any mixtures of such oil and wax components can also be used advantageously for the purposes of the present invention. It may also be advantageous to use waxes, for example cetyl palmitate, as the sole lipid component of the oily phase.

Nonpolar oils are, for example, those which are chosen from the group of branched and unbranched hydrocarbons and hydrocarbon waxes, in particular Vaseline (petrolatum), paraffin oil, squalane and squalene, polyolefins and hydrogenated polyisobutenes. Of the polyolefins, polydecenes are the preferred substances. Table 1 below lists lipids which are advantageous according to the invention as individual substances and also as a mixture with one another. The respective interfacial tensions towards water are given in the last column. It is, however, also advantageous to use mixtures of more or less polar substances and the like, provided it is ensured that the overall polarity of the oily phase lies within the claimed range.

TABLE 1

| Trade name | INCI name | (mN/m) |
|---|---|---|
| Isofol ® 14 T | Butyl Decanol + Hexyl Decanol + Hexyl Octanol + Butyl Octanol | 27.6 |
| Isofol ® 16 | Hexyl Decanol | 24.3 |
| Eutanol ® G | Octyldodecanol | 24.8 |
| Cetiol ® OE | Dicaprylyl Ether | 22.1 |
| Miglyol ® 812 | Caprylic/Capric Triglyceride | 21.3 |
| Cegesoft ® C24 | Octyl Palmitate | 23.1 |
| Isopropyl stearate | Isopropyl Stearate | 21.9 |
| Estol ® 1540 EHC | Octyl Octanoate | 30.0 |
| Finsolv ® TN | $C_{12-15}$ Alkyl Benzoate | 21.8 |
| Cetiol ® SN | Cetearyl Isononanoate | 28.6 |
| Dermofeel ® BGC | Butylene Glycol Caprylate/Caprate | 21.5 |
| Trivent ® OCG | Tricaprylin | 20.2 |
| MOD | Octyldodecyl Myristate | 22.1 |
| Cosmacol ® ETI | Di-$C_{12-13}$Alkyl Tartrate | 29.4 |
| Miglyol ® 829 | Caprylic/Capric Diglyceryl Succinate | 29.5 |
| Prisorine ® 2036 | Octyl Isostearate | 29.7 |
| Tegosoft ® SH | Stearyl Heptanoate | 28.7 |
| Abil ® Wax 9840 | Cetyl Dimethicone | 25.1 |
| Cetiol ® LC | Coco-Caprylate/Caprate | 24.8 |
| IPP | Isopropyl Palmitate | 22.5 |
| Luvitol ® EHO | Cetearyl Octanoate | 28.6 |
| Cetiol ® 868 | Octyl Stearate | 28.4 |

Basic constituents of the preparations according to the invention which may be used are:

water or aqueous solutions aqeuous ethanolic solutions natural oils and/or chemically modified natural oils and/or synthetic oils;

fats, waxes and other natural and synthetic fatty substances, preferably esters of fatty acids with alcohols of low carbon number, e.g. with isopropanol, propylene glycol or glycerol, or esters of fatty alcohols with alkanoic acids of low carbon number or with fatty acids;

alcohols, diols or polyols of low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products.

In particular, mixtures of the abovementioned solvents are used.

For the purposes of the present invention, the oily phase of the emulsions preferably consists, according to the invention, entirely of components of the type listed under point (4), although it is possible, without having to accept significant disadvantages, to choose up to 50% by weight, preferably up to 40% by weight, of the total weight of the oil components from the group of other oil components. These then can advantageously be chosen from the group of esters of saturated and/or unsaturated, branched and/or unbranched alkanecarboxylic acids having a chain length of from 3 to 30 carbon atoms and saturated and/or unsaturated, branched and/or unbranched alcohols having a chain length of from 3 to 30 carbon atoms, and from the group of esters of aromatic carboxylic acids and saturated and/or unsaturated, branched and/or unbranched alcohols having a chain length of from 3 to 30 carbon atoms. Such ester oils can then advantageously be chosen from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate, and synthetic, semisynthetic and natural mixtures of such esters, e.g. jojoba oil.

The oily phase can also be chosen advantageously from the group of branched and unbranched hydrocarbons and hydrocarbon waxes, dialkyl ethers, the group of saturated or unsaturated, branched or unbranched alcohols, and fatty acid triglycerides, namely the triglycerol esters of saturated and/or unsaturated, branched and/or unbranched alkanecarboxylic acids having a chain length of from 8 to 24, in particular 12–18, carbon atoms. The fatty acid triglyercides can, for example, be advantageously chosen from the group of synthetic, semisynthetic and natural oils, e.g. olive oil, sunflower oil, soya oil, peanut oil, rapeseed oil, almond oil, palm oil, coconut oil, palm kernel oil and the like provided the conditions required in the main claim are observed.

Fatty and/or wax components which are to be used advantageously according to the invention can be chosen from the group of vegetable waxes, animal waxes, mineral waxes and petrochemical waxes. Examples which are favourable according to the invention are candelilla wax, carnauba wax, japan wax, esparto grass wax, cork wax, guaruma wax, rice germ oil wax, sugar cane wax, berry wax, ouricury wax, montan wax, jojoba wax, shea butter, beeswax, shellac wax, spermaceti, lanolin (wool wax), uropygial grease, ceresin, ozokerite (earth wax), paraffin waxes and microcrystalline waxes provided the conditions required in the main claim are observed.

Other advantageous fatty and/or wax components are chemically modified waxes and synthetic waxes, such as, for example, those obtainable under the trade names Syncrowax HRC (glyceryl tribehenate), Syncrowax HGLC ($C_{16-36}$ fatty acid triglyceride) and Syncrowax AW 1C ($C_{18-36}$ fatty acid) from CRODA GmbH, and montan ester waxes, Sasol waxes, hydrogenated jojoba waxes, synthetic or modified beeswaxes (e.g. dimethicone copolyol beeswax and/or $C_{30-50}$ alkyl beeswax), polyalkylene waxes, polyethylene glycol waxes, but also chemically modified fats, such as, for example, hydrogenated vegetable oils (for example hydrogenated castor oil and/or hydrogenated coconut fatty glycerides), triglycerides, such as, for example, trihydroxystearin, fatty acids, fatty acid esters, and glycol esters, such as, for example, $C_{20-40}$-alkyl stearate, $C_{20-40}$-alkylhydroxystearoyl stearate and/or glycol montanate. Also advantageous are certain organosilicon compounds, which have similar physical properties to the specified fatty and/or wax components, such as, for example, stearoxytrimethylsilane provided the conditions required in the main claim are observed.

According to the invention, the fatty and/or wax components can be present either individually or as a mixture.

Any desired mixtures of such oil and wax components can also be used advantageously for the purposes of the present invention. In some instances, it can also be advantageous to use waxes, for example cetyl palmitate, as the sole lipid component of the oily phase provided the conditions required in the main claim are observed.

The oily phase is advantageously chosen from the group consisting of 2-ethylhexyl isostearate, octyldodecanol, isotridecyl isononanoate, isoeicosane, 2-ethylhexyl cocoate, $C_{12-15}$-alkyl benzoate, caprylic/capric triglyceride, dicaprylyl ether provided the conditions required in the main claim are observed.

Mixtures of $C_{12-15}$-alkyl benzoate and 2-ethylhexyl isostearate, mixtures of $C_{12-15}$-alkyl benzoate and isotridecyl isononanoate, and mixtures of $C_{12-15}$-alkyl benzoate, 2-ethylhexyl isostearate and isotridecyl isononanoate are particularly advantageous provided the conditions required in the main claim are observed.

O/W emulsions according to the invention can advantageously be prepared using customary O/W emulsifiers, if desired with the help of W/O emulsifiers or other co-emulsifiers.

O/W emulsions corresponding to the present invention comprise one or more emulsifiers, if desired advantageously chosen from the group of the following substances, which generally act as W/O emulsifiers:

Sorbitan stearate, sorbitan oleate, lecithin, glyceryl lanolate, lanolin, microcrystalline wax (Cera microcristallina) in a mixture with paraffin oil (paraffinum liquidum), ozokerite, hydrogenated castor oil, glyceryl isostearate, polyglyceryl-3 oleate, wool wax acid mixtures, wool wax alcohol mixtures, pentaerythritol isostearate, polyglyceryl-3 diisostearate, sorbitan oleate in a mixture with hydrogenating castor oil, beeswax (Cera alba) and stearic acid, sodium dihydroxycetylphosphate in a mixture with isopropyl hydroxycetyl ether, methylglucose dioleate, methylglucose dioleate in a mixture with hydroxy stearate and beeswax, mineral oil in a mixture with petrolatum and ozokerite and glyceryl oleate and lanolin alcohol, petrolatum in a mixture with ozokerite and hydrogenated castor oil and glyceryl isostearate and polyglyceryl-3 oleate, PEG-7 hydrogenated castor oil, sorbitan oleate in a mixture with PEG-2 hydrogenated castor oil, ozokerite and hydrogenated castor oil, sorbitan isostearate in a mixture with PEG-2 hydrogenated castor oil, polyglyceryl-4 isostearate, polyglyceryl-4 isostearate in a mixture with cetyldimethicone copolyol and hexyl laurate, laurylmethicone copolyol, cetyldimethicone copolyol, acrylate/$C_{10-30}$-alkyl acrylate cross polymer, sorbitan isostearate, poloxamer 101, polyglyceryl-2 dipolyhydroxystearate, polyglyceryl-3 diisostearate, polyglyceryl-4 dipolyhydroxystearate, PEG-30 dipolyhydroxystearate, diistearoylpolyglyceryl-3 diisostearate, polyglyceryl-2 dipolyhydroxystearate, polyglyceryl-3 dipolyhydroxystearate, polyglyceryl-4 dipolyhydroxystearate, polyglyceryl-3 dioleate.

If desired, O/W emulsions corresponding to the present invention comprise one or more emulsifiers, particularly advantageously chosen from the group of the following substances, which generally act as O/W emulsifiers:

Glyceryl stearate in a mixture with ceteareth-20, ceteareth-25, ceteareth-6 in a mixture with stearyl alcohol, cetylstearyl alcohol in a mixture with PEG40 castor oil and sodium cetylstearyl sulphate, triceteareth-4 phosphate, glyceryl stearate, sodium cetylstearyl suphate, lecithin trilaureth-4 phosphate, laureth-4 phosphate, stearic acid, propylene glycol stearate SE, PEG-25 hydrogenated castor oil, PEG-54 hydrogenated castor oil, PEG-6 caprylic/capric glycerides, glyceryl oleate in a mixture with propylene glycol, PEG-9 stearate, ceteth-2, ceteth-20, polysorbate 60, glyceryl stearate in a mixture with PEG-100 stearate, glyceryl myristate, glyceryl laurate, PEG-40 sorbitan peroleate, laureth-4, ceteareth-3, isostearyl glyceryl ether, cetylstearyl alcohol in a mixture with sodium cetylstearyl sulfate, laureth-23, steareth-2, glyceryl stearate in a mixture with PEG-30 stearate, PEG-40 stearate, glycol distearate, PEG-22 dodecyl glycol copolymer, polyglyceryl-2 PEG-4 stearate, ceteareth-20, methylglucose sesquistearate, steareth-10, PEG-20 stearate, steareth-2 in a mixture with PEG-8 distearate, steareth-21, steareth-20, isosteareth-20, PEG-45/dodecyl glycol copolymer, methoxy PEG-22/ dodecyl glycol copolymer, PEG-40 sorbitan peroleate, PEG-40 sorbitan perisostearate, PEG-20 glyceryl stearate, PEG-20 glyceryl stearate, PEG-8 beeswax, polyglyceryl-2 laurate, isostearyl diglyceryl succinate, stearamidopropyl-PG-dimonium chloride phosphate, glyceryl stearate SE, ceteth-20, triethyl citrate, PEG-20 methylglucose sesquistearate, ceteareth-12, glyceryl stearate citrate, cetyl phosphate, sorbitan sesquioleate, triceteareth-4 phosphate, trilaureth-4 phosphate, polyglyceryl methylglucose distearate, potassium cetyl phosphate, isosteareth-10, polyglyceryl-2 sesquiisostearate, ceteth-10, oleth-20, isoceteth-20, glyceryl stearate in a mixture with ceteareth-20, ceteareth-12, cetylstearyl alcohol and cetyl palmitate, cetylstearyl alcohol in a mixture with PEG-20 stearate, PEG-30 stearate, PEG-40 stearate, PEG-100 stearate.

For the purposes of the present invention, emulsions according to the invention, for example in the form of a skin protection cream, a skin lotion, a cosmetic milk, for example in the form of a sun protection cream or a sun protection milk, are advantageous and comprise, for example, fats, oils, waxes and/or other fatty substances, and water and one or more emulsifiers as are customarily used for this type of formulation.

The person skilled in the art is of course aware that demanding cosmetic compositions are in most cases inconceivable without the customary auxiliaries and additives. These include, for example, bodying agents, fillers, perfume, dyes, emulsifiers, additional active ingredients such as vitamins or proteins, light protection agents, stabilizers, insect repellents, alcohol, water, salts, antimicrobial, proteolytic or keratolytic substances, etc.

Corresponding requirements apply mutatis mutandis to the formulation of medicinal preparations.

For the purposes of the present invention, medicinal topical compositions generally comprise one or more medicaments in an effective concentration. For the sake of simplicity, in order to distinguish clearly between cosmetic and medicinal use and corresponding products, reference is made to the legal provisions in the Federal Republic of Germany (for example Cosmetics Directive, Foods and Drugs Act).

Accordingly, for the purposes of the present invention, cosmetic or topical dermatological compositions can, depending on their composition, be used for example as skin protection cream, cleansing milk, sunscreen lotion, nourishing cream, day or night cream, etc. If desired, it is possible and advantageous to use the compositions according to the invention as a base for pharmaceutical formulations.

It is likewise advantageous to make use of the properties according to the invention in the form of decorative cosmetics (make-up formulations).

Those cosmetic and dermatological preparations which are in the form of a sunscreen are also favourable. In addition to the active ingredient used according to the invention, these also preferably comprise at least one UVA filter substance and/or at least one UVB filter substance and/or at least one inorganic pigment.

However, it is also advantageous for the purposes of the present invention to provide cosmetic and dermatological preparations whose main purpose is not protection against sunlight, but which nevertheless contain anti-UV substances. Thus, for example, UV-A and UV-B filter substances are usually incorporated into day creams.

Preparations according to the invention can advantageously comprise substances which absorb UV radiation in the UVB region, the total amount of filter substances being, for example, from 0.1% by weight to 30% by weight, preferably from 0.5 to 10% by weight, in particular from 1 to 6% by weight, based on the total weight of the preparations.

The UVB filters can be oil-soluble or water-soluble. Examples of oil-soluble substances which may be mentioned are:

3-benzylidenecamphor and derivatives thereof, e.g. 3-(4-methylbenzylidene)camphor, 4-aminobenzoic acid derivatives, preferably 2-ethylhexyl 4-(dimethylamino)benzoate, amyl 4-(dimethylamino) benzoate;

esters of cinnamic acid, preferably 2-ethylhexyl 4-methoxycinnamate, isopentyl 4-methoxycinnamate;

esters of salicylic acid, preferably 2-ethylhexyl salicylate, 4-isopropylbenzyl salicylate homomenthyl salicylate;

derivatives of benzophenone, preferably 2-hydroxy-4-methoxybenzophenone, 2-hydroxy-4-methoxy-4'-methylbenzophenone, 2,2'-dihydroxy-4-methoxybenzphenone;

esters of benzalmalonic acid, preferably di(2-ethylhexyl) 4-methoxybenzalmalonate;

2,4,6-trianilino(p-carbo-2'-ethyl-1'-hexyloxy)-1,3,5-triazine.

Advantageous water-soluble substances are:

2-phenylbenzimidazole-5-sulphonic acid and salts thereof, for example sodium, potassium or triethanolammonium salts, sulphonic acid derivatives of benzophenones, preferably 2-hydroxy-4-methoxy-benzophenone-5-sulphonic acid and its salts;

sulphonic acid derivatives of 3-benzylidenecamphor, such as, for example, 4-(2-oxo-3-bornylidenemethyl) benzenesulphonic acid, 2-methyl-5-(2-oxo-3-bornylidenemethyl-sulphonic acid and its salts.

The list of given UVB filters which can be used according to the invention is of course not intended to be limiting.

It can also be advantageous to use UVA filters that are usually present in cosmetic and/or dermatological preparations in preparations according to the invention. Such filter substances are preferably derivatives of dibenzoylmethane, in particular 1-(4'-tert-butylphenyl)-3-(4'-methoxyphenyl) propane-1,3-dione and 1-phenyl-3-(4'-isopropylphenyl)- propane-1,3-dione. Preparations which comprise these combinations are also provided by the invention. It is possible to use the same amounts of UVA filter substances which were given for UVB filter substances.

For the purposes of the present invention, cosmetic and/or dermatological preparations can also comprise inorganic pigments which are usually used in cosmetics for protecting the skin against UV radiation. These are oxides of titanium, zinc, iron, zirconium, silicon, manganese, aluminium, cerium and mixtures thereof, and modifications in which the oxides are the active agents. Particular preference is given to pigments based on titanium dioxide It is possible to use the quantities given for the above combinations.

The cosmetic and dermatological preparations according to the invention can comprise cosmetic active ingredients, auxiliaries and/or additives as are usually used in such preparations, for example antioxidants, preservatives, bactericides, perfumes, antifoams, dyes, pigments which have a colouring effect, thickeners, surfactants, emulsifiers, emollients, moisturizers and/or humectants, fats, oils, waxes or other usual constituents of a cosmetic or dermatological formulation, such as alcohols, polyols, polymers, foam stabilizers, electrolytes, organic solvents or silicone derivatives.

For the purposes of the present invention, it is advantageous to add other anti-irritative or anti-inflammatory active ingredients to the preparations, in particular batyl alcohol ($\alpha$-octadecyl glyceryl ether), selachyl alcohol ($\alpha$-9-octadecenyl glyceryl ether), chimyl alcohol ($\alpha$-hexadecyl glyceryl ether), bisabolol and/or panthenol.

It is likewise advantageous to add conventional antioxidants to the preparations for the purposes of the present invention. According to the invention, favourable antioxidants can be any antioxidants which are suitable or customary for cosmetic and/or dermatological applications.

The antioxidants are advantageously selected from the group consisting of amino acids (for example glycine, histidine, tyrosine, tryptophan) and derivatives thereof, imidazoles (e.g. urocanic acid) and derivatives thereof, peptides such as D,L-carnosine, D-carnosine, L-carnosine and derivatives thereof (e.g. anserine), carotenoids, carotenes (e.g. $\alpha$-carotene, $\beta$-carotene, $\psi$-lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, $\gamma$-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulphoximine compounds (e.g. buthionine sulphoximines, homocysteine sulphoximine, buthionine sulphones, penta-, hexa-, heptathionine sulphoximine) in very small tolerated doses (e.g. pmol to $\mu$mol/kg), also (metal) chelating agents (e.g. $\alpha$-hydroxy fatty acids, palmitic acid, phytic acid, lactoferrin), $\alpha$-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. $\gamma$-linolenic acid, linoleic acid, oleic acid), folic acid and derivatives thereof, furfurylidenesorbitol and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate) and coniferyl benzoate of benzoin, rutinic acid and derivatives thereof, $\alpha$-glycosylrutin, ferulic acid, furfurylideneglucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, zinc and derivatives thereof (e.g. ZnO, $ZnSO_4$), selenium and derivatives thereof (e.g. selenium methionine), stilbenes and derivatives thereof (e.g. stilbene oxide, trans-stilbene oxide) and the derivatives (salts, esters, ethers, sugars, nucleotides, nucleosides, peptides and lipids) of said active ingredients which are suitable according to the invention.

The amount of antioxidants (one or more compounds) in the preparations is preferably from 0.001 to 30% by weight, particularly preferably 0.05–20% by weight, in particular 1–10% by weight, based on the total weight of the preparation.

If vitamin E and/or derivatives thereof are used as the antioxidant(s), it is advantageous to choose their respective concentrations from the range 0.001–10% by weight, based on the total weight of the formulation.

The preparations according to the present invention can also be used as bases for cosmetic or dermatological deodorants or antiperspirants. All active ingredients which are common for deodorants or antiperspirants can be used advantageously, for example odour maskers such as the customary perfume constituents, odour absorbers, for example the phyllosilicates described in laid-open patent specification DE-P 40 09 347, and of these, in particular montmorillonite, kaolinite, ilite, beidellite, nontronite, saponite, hectorite, bentonite, smectite, and also, for example, zinc salts of ricinoleic acid.

Antibacterial agents are likewise suitable for incorporation into the preparations according to the invention. Advantageous substances are, for example, 2,4,4'-trichloro-2'-hydroxydiphenyl ether (Irgasan), 1,6-di(4-chlorophenylbiguanido)hexane (chlorhexidine), 3,4,4'-trichlorocarbanilide, quaternary ammonium compounds, oil of cloves, mint oil, oil of thyme, triethyl citrate, farnesol (3,7,11-trimethyl-2,6,10-dodecatrien-1-ol) and the active ingredients or active ingredient combinations described in laid-open patent specifications DE-37 40 186, DE-39 38 140, DE42 04 321, DE42 29 707,DE43 09 372, DE44 11 664, DE-195 41 967, DE-195 43 695, DE-195 43 696, DE-19547 160, DE-196 02 108, DE-196 02 110, DE-196 02 111, DE-196 31 003, DE-196 31 004 and DE-196 34 019 and the patent specifications DE42 29 737, DE42 37 081, DE43 24 219, DE44 29 467, DE44 23 410 and DE-195 16 705. Sodium hydrogencarbonate can also be used advantageously.

The amount of such active ingredients (one or more compounds) in the preparations according to the invention is preferably from 0.001 to 30% by weight, particularly preferably 0.05–20% by weight, in particular 1–10% by weight, based on the total weight of the preparation.

For the purposes of the present invention, the aqueous phase of the cosmetic preparations can also have gel character which, in addition to an effective content of the substances used according to the invention and the solvents used customarily therefor, preferably water, also comprises other organic thickeners, e.g. gum arabic, xanthan gum, sodium alginate, starch and starch derivatives (e.g. distarch phosphate), cellulose, cellulose derivatives, preferably methylcellulose, hydroxymethylcellulose, hydroxyethylcellulose, hydroxypropylcellulose, hydroxypropylmethylcellulose or inorganic thickeners, e.g. aluminium silicates such as, for example, organically modified and also unmodified hectorites, bentonites or the like, or a mixture of polyethylene glycol and polyethylene glycol stearate or distearate. The thickener is present in the gel, for example in an amount between 0.1 and 30% by weight, preferably between 0.5 and 15% by weight.

It can also be advantageous to add interface- or surface-active agents according to the invention to preparations, for example cationic emulsifiers such as, in particular, quaternary surfactants.

Quaternary surfactants contain at least one N-atom which is covalently bonded to 4 alkyl or aryl groups. Irrespective of the pH, this leads to a positive charge. Alkylbetaine, alkylamidopropylbetaine and alkylamidopropylhydroxysultaine are advantageous. The cationic surfactants used according to the invention can also preferably be chosen from the group of quaternary ammonium compounds, in particular benzyltrialkylammonium chlorides or bromides, such as, for example, benzyldimethylstearylammonium chloride, and also alkyltrialkylammonium salts, for example cetyltrimethylammonium chloride or bromide, alkyldimethylhydroxyethylammonium chlorides or bromides, dialkyldimethylammonium chlorides or bromides, alkylamidoethyltrimethylammonium ether sulphates, alkylpyridinium salts, for example lauryl- or cetylpyridinium chloride, imidazoline derivates and compounds having a cationic character such as amine oxides, for example alkyldimethylamine oxides or alkylaminoethyldimethylamine oxide. In particular, cetyltrimethylammonium salts are to be used advantageously.

It is also advantageous to use cationic polymers (e.g. Jaguar® C 162 [hydroxypropyl guar hydroxypropyltrimonium chloride] or modified magnesium aluminium silicates (e.g. quaternium-18 hectorite, which is obtainable, for example, under the trade name Bentone® 38 from Rheox, or stearalkonium hectorite, which is obtainable, for example, under the trade name Softisan® Gel from Hüls AG).

Preparations according to the invention can advantageously also comprise oil thickeners in order to improve the tactile properties of the emulsion and the stick consistency. Advantageous oil thickeners for the purposes of the present invention are, for example, other solids, such as, for example, hydrophobic silicon oxides of the Aerosil® type, which are obtainable from Degussa AG. Advantageous Aerosil® products are, for example, Aerosil® OX50, Aerosil® 130, Aerosil® 150, Aerosil® 200, Aerosil® 300 Aerosil® 380, Aerosil® MOX 80, Aerosil® MOX 170, Aerosil® COK 84, Aerosil® R 202, Aerosil® R 805, Aerosil® R 812, Aerosil® R 972, Aerosil® R 974 and/or Aerosil® R976.

In addition, so-called metal soaps (i.e. the salts of higher fatty acids with the exception of the alkali metal salts) are also advantageous oil thickeners for the purposes of the present invention, such as, for example, aluminium stearate, zinc stearate and/or magnesium stearate.

It is likewise advantageous to add amphoteric or zwitterionic surfactants (e.g. cocoamidopropylbetaine) and moisturizers (e.g. betaine) to preparations according to the invention. Examples of amphoteric surfactants which are to be used advantageously are acyl-/dialkylethylenediamine, for example sodium acylamphoacetate, disodium acylamphodipropionate, disodium alkylamphodiacetate, sodium acylamphohydroxypropylsulphonate, disodium acylamphodiacetate and sodium acylamphopropionate, N-alkylamino acids, for example aminopropylalkylglutamide, alkylaminopropionic acid, sodium alkylimidodipropionate and lauroamphocarboxyglycinate.

The amount of interface- or surface-active substances (one or more compounds) in the preparations according to the invention is preferably from 0.001 to 30% by weight, particularly preferably 0.05–20% by weight, in particular 1–10% by weight, based on the total weight of the preparation.

Preparations according to the invention can also comprise active ingredients (one or more compounds) which are chosen from the group: acetylsalicylic acid, atropine, azulene, hydrocortisone and derivatives thereof, e.g. hydrocortisone-17 valerate, vitamins, e.g. ascorbic acid and derivatives therof, vitamins of the B and D series, very favourably vitamin $B_1$, vitamin $B_{12}$ and vitamin $D_1$, but also bisabolol, unsaturated fatty acids, namely the essential fatty acids (often also called vitamin F), in particular γ-linolenic acid, oleic acid, eicosapentaenoic acid, docosahexaenoic acid and derivatives thereof, chloramphenicol, caffeine, prostaglandins, thymol, camphor, extracts or other products of a vegetable or animal origin, e.g. evening primrose oil, starflower oil or currant seed oil, fish oils, cod-liver oil or also ceramides and ceramide-like compounds, etc. It is also advantageous to choose the active ingredients from the group of refatting substances, for example Purcellin oil, Eucerit® and Neocerit®.

The amount of such active ingredients (one or more compounds) in the preparations according to the invention is preferably from 0.001 to 30% by weight, particularly preferably 0.05–20% by weight, in particular 1–10% by weight, based on the total weight of the preparation.

The examples below serve to illustrate the present invention.

EXAMPLE 1

|  | % by weight |
| --- | --- |
| Stearic acid/palmitic acid | 2.00 |
| PEG-40 stearate | 2.00 |
| Glyceryl stearate | 2.00 |
| Cetylstearyl alcohol | 3.00 |
| Hydrogenated polyisobutene | 7.00 |
| Petrolatum | 4.00 |
| Cyclomethicone | 9.00 |
| Glyceryl lanolate | 2.00 |
| Glycerol | 4.00 |
| Perfume, preservatives, dyes, antioxidants etc. | q.s. |
| Water | ad 100.00 |
| pH adjusted to | 6.5 |

EXAMPLE 2

|  | % by weight |
| --- | --- |
| Stearic acid/palmitic acid | 1.20 |
| PEG-40 stearate | 2.00 |
| Glyceryl stearate | 4.00 |
| Cetylstearyl alcohol | 3.00 |
| Hydrogenated polyisobutene | 10.00 |
| Cyclomethicone | 10.00 |
| Glyceryl lanolate | 2.00 |
| Glycerol | 4.00 |
| Perfume, preservatives, dyes, antioxidants etc. | q.s. |
| Water | ad 100.00 |
| pH adjusted to | 6.5 |

EXAMPLE 3

|  | % by weight |
|---|---|
| Stearic acid/palmitic acid | 1.20 |
| PEG-40 stearate | 2.00 |
| Glyceryl stearate | 6.00 |
| Cetylstearyl alcohol | 2.50 |
| Hydrogenated polyisobutene | 8.00 |
| Petrolatum | 2.00 |
| Cyclomethicone | 9.00 |
| Glyceryl lanolate | 2.00 |
| Glycerol | 4.00 |
| Perfume, preservatives, dyes, antioxidants etc. | q.s. |
| Water | ad 100.00 |
| pH adjusted to | 6.5 |

EXAMPLE 4

|  | % by weight |
|---|---|
| Stearic acid/palmitic acid | 1.20 |
| PEG-100 stearate | 1.20 |
| Glyceryl stearate | 3.60 |
| Cetylstearyl alcohol | 3.00 |
| Hydrogenated polyisobutene | 9.00 |
| Petrolatum | 2.00 |
| Cyclomethicone | 7.00 |
| Dimethicone | 3.00 |
| Glyceryl lanolate | 2.00 |
| Glycerol | 4.00 |
| Perfume, preservatives, dyes, antioxidants etc. | q.s. |
| Water | ad 100.00 |
| pH adjusted to | 7.0 |

EXAMPLE 5

|  | % by weight |
|---|---|
| Stearic acid/palmitic acid | 1.20 |
| PEG-20 stearate | 1.20 |
| Glyceryl stearate | 3.60 |
| Cetylstearyl alcohol | 3.00 |
| Hydrogenated polyisobutene | 9.00 |
| Petrolatum | 2.00 |
| Cyclomethicone | 5.00 |
| Dimethicone | 5.00 |
| Glyceryl lanolate | 5.00 |
| Glycerol | 10.00 |
| Perfume, preservatives, dyes, antioxidants etc. | q.s. |
| Water | ad 100.00 |
| pH adjusted to | 6.5 |

EXAMPLE 6

|  | % by weight |
|---|---|
| Stearic acid/palmitic acid | 1.20 |
| PEG-40 stearate | 1.20 |
| Glyceryl stearate | 3.60 |
| Cetylstearyl alcohol | 3.00 |
| Hydrogenated polyisobutene | 8.00 |
| Paraffinum liquidum | 5.00 |
| Petrolatum | 2.00 |
| Cyclomethicone | 10.00 |
| Glyceryl lanolate | 2.00 |
| Glycerol | 10.00 |
| Perfume, preservatives, dyes, antioxidants etc. | q.s. |
| Water | ad 100.00 |
| pH adjusted to | 7.0 |

EXAMPLE 7

|  | % by weight |
|---|---|
| Stearic acid/palmitic acid | 1.20 |
| PEG-40 stearate | 1.20 |
| Glyceryl stearate | 3.60 |
| Cetylstearyl alcohol | 3.00 |
| Hydrogenated polyisobutene | 8.00 |
| Polydecene | 6.00 |
| Petrolatum | 4.00 |
| Cyclomethicone | 10.00 |
| Glyceryl lanolate | 2.00 |
| Glycerol | 5.00 |
| Perfume, preservatives, dyes, antioxidants etc. | q.s. |
| Water | ad 100.00 |
| pH adjusted to | 7.0 |

EXAMPLE 8

|  | % by weight |
|---|---|
| Stearic acid/palmitic acid | 1.20 |
| PEG-40 stearate | 2.00 |
| Glyceryl stearate | 4.00 |
| Cetearyl alcohol | 3.00 |
| Hydrogenated polyisobutene | 9.00 |
| Polydecene | 5.00 |
| Caprylic/capric triglycerides | 5.00 |
| Petrolatum | 1.00 |
| Cyclomethicone | 4.00 |
| Glyceryl lanolate | 2.00 |
| Glycerol | 3.00 |
| Perfume, preservatives, dyes, antioxidants etc. | q.s. |
| Water | ad 100.00 |
| pH adjusted to | 6.0 |

EXAMPLE 9

|  | % by weight |
|---|---|
| Stearic acid/palmitic acid | 1.20 |
| PEG-40 stearate | 2.00 |
| Glyceryl stearate | 4.00 |
| Cetylstearyl alcohol | 3.00 |
| Hydrogenated polyisobutene | 12.00 |
| Polydecene | 4.00 |
| Cyclomethicone | 5.00 |
| Glyceryl lanolate | 2.00 |
| Glycerol | 3.00 |
| Octyl methoxycinnamate | 3.00 |

-continued

| | % by weight |
|---|---|
| Benzophenone-3 | 2.00 |
| Octyl salicylate | 1.00 |
| Perfume, preservatives, NaOH, dyes, antioxidants etc. | q.s. |
| Water | ad 100.00 |
| pH adjusted to | 7.0 |

EXAMPLE 10

| | % by weight |
|---|---|
| Stearic acid/palmitic acid | 1.00 |
| PEG-100 stearate | 2.00 |
| Glyceryl stearate | 4.00 |
| Cetylstearyl alcohol | 3.00 |
| Hydrogenated polyisobutene | 9.00 |
| Octyldodecanol | 3.50 |
| Dimethicone | 10.00 |
| Myristyl myristate | 4.00 |
| Glycerol | 3.00 |
| Perfume, preservatives, dyes, antioxidants etc. | q.s. |
| Water | ad 100.00 |
| pH adjusted to | 7.0 |

EXAMPLE 11

| | % by weight |
|---|---|
| Stearic acid/palmitic acid | 1.00 |
| PEG-100 stearate | 2.00 |
| Glyceryl stearate | 4.00 |
| Cetylstearyl alcohol | 3.00 |
| Hydrogenated polyisobutene | 0.50 |
| Dimethicone | 5.00 |
| Cyclomethicone | 15.00 |
| Myristyl myristate | 4.00 |
| Glycerol | 3.00 |
| Perfume, preservatives, dyes, antioxidants etc. | q.s. |
| Water | ad 100.00 |
| pH adjusted to | 7.0 |

What is claimed is:

1. Cosmetic and dermatological preparations in the form of O/W emulsions, consisting essentially of
   (1) 0.1 up to 5% by weight, based on the total weight of the preparations, of one or more $C_{14}$–$C_{22}$-fatty acids,
   (2) 0.2 up to 10% by weight, based on the total weight of the preparations, of one or more mono- and/or diglycerides of fatty acids,
   (3) 0.1 up to 5% by weight, based on the total weight of the preparations, of one or more ethoxylated fatty acid esters,
   where the sum of (1), (2) and (3) is at most 12% by weight, based on the total weight of the preparations,
   (4) 0.5 up to 10% by weight, based on the total weight of the preparations, of one or more nonpolar lipids,
   (5) 0.5 up to 7.5% by weight, based on the total weight of the preparations, of one or more fatty alcohols
   (6) 0.5 up to 7.5% by weight, based on the total weight of the preparations, of one or more lipophilic bodying agents having a melting point or dropping point of $\geq 30°$ C.
   (7) where the total lipid phase can comprise up to 40% by weight of polar lipids, based on the total weight of the lipid phase.

2. Cosmetic and dermatological preparations according to claim 1, wherein
   (1) 0.5 up to 1.0% by weight, based on the total weight of the preparations, of one or more $C_{14}$–$C_{22}$-fatty acids.

3. Cosmetic and dermatological preparations according to claim 1, wherein
   (2) 2.5 up to 3.0% by weight, based on the total weight of the preparations, of one or more mono- and/or diglycerides of fatty acids.

4. Cosmetic and dermatological preparations according to claim 1, wherein
   (3) 1.0 up to 1.5% by weight, based on the total weight of the preparations, of one or more ethoxylated fatty acid esters.

5. Cosmetic and dermatological preparations according to claim 1, wherein
   (2) up to 10% by weight, based on the total weight of the preparations, of glyceryl stearate.

6. Cosmetic and dermatological preparations according to claim 1, wherein
   (3) up to 5% by weight, based on the total weight of the preparations, of one or more ethoxylated fatty acid esters selected from the group consisting of polyethylene glycol-20 (PEG-20) to polyethylene glycol-100 (PEG-100) stearates.

7. Cosmetic or dermatological preparations according to claim 1, wherein
   (4) 0.5 up to 10% by weight, based on the total weight of the preparations, of one or more nonpolar lipids, selected from the group consisting of mineral oil and/or mineral waxes.

8. Cosmetic and dermatological preparations according to claim 1, wherein
   (5) 2.0 up to 3.0% by weight, based on the total weight of the preparations, of one or more fatty alcohols.

9. Cosmetic and dermatological preparations according to claim 1, wherein
   (6) 1.5 up to 2.5% by weight, based on the total weight of the preparations, of one or more, lipophilic bodying agents having a melting point or dropping point of $\geq 30°$ C.

10. Cosmetic or dermatological preparations according to claim 7, wherein the mineral oil and/or mineral waxes is petrolatum.

* * * * *